US010582991B2

(12) United States Patent
Kleppen et al.

(10) Patent No.: US 10,582,991 B2
(45) Date of Patent: Mar. 10, 2020

(54) POWER TOOTHBRUSH WITH ADDED INERTIA RESONANT SYSTEM (71) Applicant: KONINKLIJKE PHILIPS N.V., Eindhoven (NL)

(72) Inventors: Lane Evan Kleppen, Seattle, WA (US); Scott Robert Wills, Shoreline, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 341 days.

(21) Appl. No.: 15/325,898

(22) PCT Filed: Jul. 15, 2015

(86) PCT No.: PCT/IB2015/055355
§ 371 (c)(1),
(2) Date: Jan. 12, 2017

(87) PCT Pub. No.: WO2016/009368
PCT Pub. Date: Jan. 21, 2016

(65) Prior Publication Data
US 2017/0156836 A1 Jun. 8, 2017

Related U.S. Application Data (60) Provisional application No. 62/025,531, filed on Jul. 17, 2014.

(51) Int. Cl.
A61C 17/34 (2006.01)
A61C 17/32 (2006.01)
(Continued)

(52) U.S. Cl.
CPC .......... *A61C 17/3418* (2013.01); *A61C 17/32* (2013.01); *A61C 17/34* (2013.01);
(Continued)

(58) Field of Classification Search
CPC ....... A46B 13/02; A46B 13/023; A61C 17/22; A61C 17/32; A61C 17/34; A61C 17/3409;
(Continued)

(56) References Cited

U.S. PATENT DOCUMENTS 3,284,649 A * 11/1966 Barlow ................. G04C 15/00
192/223
3,676,218 A * 7/1972 Sawyer .............. A61C 17/3481
134/1

(Continued)

FOREIGN PATENT DOCUMENTS

CN 1510822 A 7/2004
EP 0893106 A2 1/1999
EP 1329203 A1 7/2003
(Continued)

*Primary Examiner* — Mark Spisich (57) ABSTRACT

An added inertia resonant system (12) for a power toothbrush (10) comprises a drive shaft (16), a drive system (22), and at least one inertial weight member (24). The drive shaft (16) has a principal axis (26) that defines a center of rotation. The drive system (22) imparts a reciprocating motion to the drive shaft (16) about the principal axis(26). The at least one inertial weight member (24) couples to the drive shaft (16) and comprises a planar material having a complex shape balanced along an x-, y-and z-axis to enable the drive system (22) to achieve low power, high amplitude motion of the drive shaft (16) when placed under user loading. A method for providing added inertia in a resonant system for a power toothbrush is also disclosed.

8 Claims, 6 Drawing Sheets (51) Int. Cl.
- *F16F 7/10* (2006.01)
- *H02K 7/14* (2006.01)
- *H02K 7/02* (2006.01)
- *F16F 15/30* (2006.01)
- *F16F 15/315* (2006.01)
- *A46B 13/02* (2006.01)

(52) U.S. Cl.
CPC ............... *A46B 13/023* (2013.01); *F16F 7/10* (2013.01); *F16F 15/30* (2013.01); *F16F 15/3153* (2013.01); *H02K 7/02* (2013.01); *H02K 7/145* (2013.01)

(58) Field of Classification Search
CPC .. A61C 17/3418; A61C 17/3481; H02K 7/02; H02K 7/04; H02K 7/14; H02K 7/145; F16C 2380/28; F16C 236/155; F16C 15/00; F16F 7/10; F16F 7/1022; F16F 9/504; F16F 15/30; F16F 15/315; F16F 15/3153
USPC ............ 15/22.1, 22.2, 22.4; 310/74; 188/378–380; 74/572.2, 572.4, 74/574.2–574.4
See application file for complete search history.

(56) References Cited

U.S. PATENT DOCUMENTS

| | | | |
|---|---|---|---|
| 5,934,908 A * | 8/1999 | Woog | A61C 17/20 15/167.1 |
| 6,401,288 B1 | 6/2002 | Porper et al. | |
| 6,833,639 B2 | 12/2004 | Lau et al. | |
| 2003/0029269 A1* | 2/2003 | Gabrys | F16F 15/30 74/572.11 |
| 2004/0119344 A1 | 6/2004 | Lau et al. | |
| 2005/0039569 A1* | 2/2005 | Chentemirov | F16F 15/30 74/570.1 |
| 2008/0209650 A1 | 9/2008 | Brewer et al. | |
| 2011/0214239 A1 | 9/2011 | Kagami et al. | |

FOREIGN PATENT DOCUMENTS

| | | |
|---|---|---|
| EP | 1696539 A1 | 8/2006 |
| EP | 2246009 A1 | 11/2010 |
| FR | 1171337 | 1/1959 |
| JP | 64-21244 * | 1/1989 |
| JP | 2000237683 A | 9/2000 |
| JP | 2003080168 A | 3/2003 |
| JP | 2009219756 A | 10/2009 |
| JP | 2010051907 A | 3/2010 |
| WO | 03054414 A1 | 7/2003 |
| WO | 2011077287 A1 | 6/2011 |

* cited by examiner

POWER TOOTHBRUSH WITH ADDED INERTIA RESONANT SYSTEM

CROSS-REFERENCE TO PRIOR APPLICATIONS

This application is the U.S. National Phase application under 35 U.S.C. § 371 of International Application No., filed on PCT/IB2015/055355, filed on Jul. 15, 2015, which claims the benefit of U.S. Provisional Patent Application No. 62/025,531, filed on Jul. 17, 2014. These applications are hereby incorporated by reference herein.

The present embodiments relate generally to power toothbrushes and more particularly, to a power toothbrush with added inertia resonant system and a method of implementing an added inertia resonant system in a power toothbrush.

Motor designs used as resonant systems in electric toothbrushes are generally known. In addition, use of inertial weight to overcome mechanical instabilities is generally well-known (e.g. fly-wheels). However, such motor designs with known resonant systems for electric toothbrushes undesirably lose amplitude when placed under user load.

For example, an impediment to successful implementation of an improved power toothbrush is the failure to deliver low power yet high amplitude motion through an attached brush-head when placed under user loading.

Accordingly, it would be desirable to provide a resonant system that does not lose amplitude when placed under user load. An improved method and apparatus for overcoming the problems in the art is thus desired.

In accordance with one aspect, a power toothbrush with added inertia resonant system comprises added inertia that is effective in controlling the amplitude of motion under load conditions.

In accordance with another aspect, an added inertia resonant system for a power toothbrush comprises a drive shaft having a principal axis that defines a center of rotation; a drive system configured to impart a reciprocating motion to said drive shaft about the principal axis; and at least one inertial weight member coupled to the drive shaft. The at least one inertial weight member comprises a single planar material having a complex shape balanced along an x-, y- and z-axis to enable the drive system to achieve low power, high amplitude motion of the drive shaft when placed under user loading. In one embodiment, the low power, high amplitude motion comprises a power on the order of <4 W and an amplitude on the order of up to 20 degrees full motion about the center of rotation. In another embodiment, the low power comprises a range of 1 W-4 W.

In one embodiment, the complex shape of the inertial weight includes an inner portion, a first outer portion extending from the inner portion in a first direction, and a second outer portion extending from the inner portion in a second direction, opposite the first direction.

In another embodiment, the inner portion includes a mounting aperture having a principal diameter configured for being mounted, e.g., via a press fit, onto the drive shaft along the principal axis. The mounting aperture further includes at least one attachment feature configured for coupling the inertial weight member via a press fit onto a complementing feature of the drive shaft in a given radial orientation with respect to the principal axis. In a further embodiment, the at least one attachment feature comprises four equally spaced features about an inner perimeter of the mounting aperture in the inner portion of the inertial weight member.

According to another embodiment, the first outer portion of the complex shape comprises a first additional weight located between a first and second radial distance away from the center of rotation. The second outer portion of the complex shape comprises a counter-balanced additional weight located between the first radial distance and a third radial distance, wherein the third radial distance is greater than the second radial distance around the z-axis. Furthermore, a perimeter of the first outer portion at the second radial distance is greater than a perimeter of the second outer portion at the third radial distance.

In another embodiment, the inertial weight member comprises stainless steel. In a further embodiment, the at least one inertial weight member is coupled to the drive shaft at a location of the drive shaft within one selected from the group consisting of a front portion, a middle portion, and a rear portion of the drive system. In addition, the at least one inertial weight member can further comprise recesses and dimples formed in or on planar surfaces of the at least one inertial weight member that co-locate and secure a plurality of inertial weight members together as a lamination to increase a total weight for a desired total inertial mass.

In yet another embodiment, a power toothbrush, comprises the added inertia resonant system, as described above, and a brush head member adapted for being coupled in a removable fashion to a front portion of the drive shaft.

According to another embodiment, a method of providing added inertia in a resonant system for a power toothbrush comprises: providing a drive shaft having a principal axis that defines a center of rotation; configuring a drive system to impart a reciprocating motion to said drive shaft about the principal axis; and coupling at least one inertial weight member to the drive shaft. The at least one inertial weight member comprises a single planar material having a complex shape balanced along an x-, y- and z-axis to enable the drive system to achieve low power, high amplitude motion of the drive shaft when placed under user loading. The complex shape includes an inner portion, a first outer portion extending from the inner portion in a first direction, and a second outer portion extending from the inner portion in a second direction, opposite the first direction.

In a further embodiment, the inner portion includes a mounting aperture having a principal diameter configured for being mounted, e.g., via a press fit, onto the drive shaft along the principal axis. The mounting aperture further includes at least one attachment feature configured for coupling the inertial weight member via a press fit onto a complementing feature of the drive shaft in a given radial orientation with respect to the principal axis.

In a still further embodiment, the first outer portion of the complex shape comprises a first additional weight located between a first and second radial distance away from the center of rotation. The second outer portion of the complex shape comprises a counter-balanced additional weight located between the first radial distance and a third radial distance, wherein the third radial distance is greater than the second radial distance around the z-axis, and further wherein a perimeter of the first outer portion at the second radial distance is greater than a perimeter of the second outer portion at the third radial distance.

In another embodiment, the added inertia in a resonant system for a power toothbrush further comprises a resilient mount and a frame. The drive system is coupled to the frame via the resilient mount. The resilient mount includes rotational displacement cogging stop surfaces. In addition, the first outer portion of the complex shape further comprises first and second rotation stop surfaces, wherein the first and second rotation stop surfaces are configured for engagement with cogging stop surfaces of the resilient mount to limit a rotational displacement of the drive shaft within a desired range.

The embodiments of the present disclosure advantageously solve the problem of delivering low power, high amplitude motion through an attached brush-head when placed under user loading.

Still further advantages and benefits will become apparent to those of ordinary skill in the art upon reading and understanding the following detailed description.

The embodiments of the present disclosure may take form in various components and arrangements of components, and in various steps and arrangements of steps. Accordingly, the drawings are for purposes of illustrating the various embodiments and are not to be construed as limiting the embodiments. In the drawing figures, like reference numerals refer to like elements. In addition, it is to be noted that the figures may not be drawn to scale.

The embodiments of the present disclosure and the various features and advantageous details thereof are explained more fully with reference to the non-limiting examples that are described and/or illustrated in the drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the present disclosure. The examples used herein are intended merely to facilitate an understanding of ways in which the embodiments of the present may be practiced and to further enable those of skill in the art to practice the same. Accordingly, the examples herein should not be construed as limiting the scope of the embodiments of the present disclosure, which is defined solely by the appended claims and applicable law.

It is understood that the embodiments of the present disclosure are not limited to the particular methodology, protocols, devices, apparatus, materials, applications, etc., described herein, as these may vary. It is also to be understood that the terminology used herein is used for the purpose of describing particular embodiments only, and is not intended to be limiting in scope of the embodiments as claimed. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which the embodiments of the present disclosure belong. Preferred methods, devices, and materials are described, although any methods and materials similar or equivalent to those described herein can be used in the practice or testing of the embodiments.

According to one embodiment, a power toothbrush with an added inertia resonant system is applicable for use as a resonant system that includes a shaft, drive stator, laminations, and magnets per power toothbrush motor. The power toothbrush motor, which operates in a reciprocating manner, can be instituted in various power toothbrush designs for delivering brushing motion. The addition of inertial weight to the reciprocating motion has been shown to be less susceptible to low amplitude motion and high power consumption when under user loading, due in part to the added user loading being a lower percentage of the weight/inertia of the drive system.

According to one embodiment, a balanced weight is attached to the reciprocating motor shaft. Various embodiments are discussed herein, for example, the balanced weight is located on the reciprocating motor shaft above the main drive body, inside the main drive body, and/or behind the main drive body. The weight is balanced on the x, y, and z axis so as to not introduce any unbalanced loading or vibration due to an introduced imbalance.

According to an embodiment of the present disclosure, the balanced weight comprises a given material that will not interfere with magnetic properties of the drive motor or drive system, yet have density enough to allow the design to be sized in such a manner to make it effective in the use of hand-held power toothbrush designs. In one embodiment, a single inertia weight is configured for being mechanically pressed onto the shaft of the drive system. The inertia weight is characterized in that the x, y, and z axis are balanced. Additional parts could be stacked as laminations so as to increase the weight as desired to balance individual systems. In one embodiment, the inertial weight includes stainless steel laminations located at the rear of the drive system; however, the material and location of the inertia weight could vary per design as needed.

Figure 1:
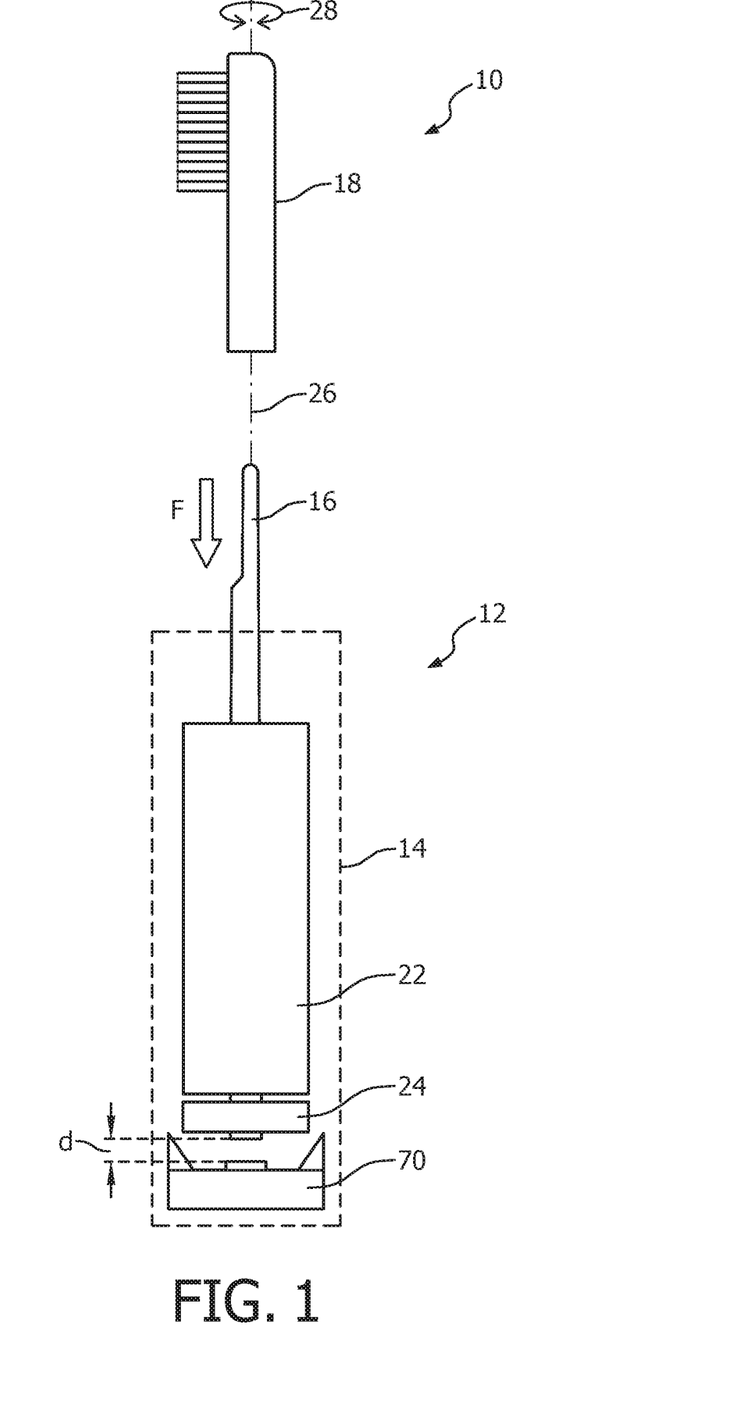
FIG. 1 is an exploded diagram view of a power toothbrush with added inertia resonant system according to an embodiment of the present disclosure.

Referring now to FIG. 1, there is shown an exploded diagram view of a power toothbrush 10 with added inertia resonant system 12 according to one embodiment of the present disclosure. The power toothbrush 10 includes a handle 14 for being gripped by a user during brushing of his or her teeth. The added inertia resonant system 12 is enclosed within handle 14, with the exception of one end of drive shaft 16 which is configured for attachment of a brush-head 18. The added inertia resonant system 12 comprises the drive shaft 16, a drive system 22 and at least one inertial weight member 24. The drive shaft 16 has a principal axis 26 that defines a center of rotation. The drive system 22 is configured to impart a reciprocating motion, generally indicated by arrow 28, to the drive shaft 16 about the principal axis 26. The at least one inertial weight member 24 is coupled to the drive shaft 16, as will be discussed further herein below.

In one embodiment, the at least one inertial weight member 24 comprises a single planar material having a complex shape balanced along an x-, y- and z-axis to enable the drive system 22 to achieve low power, high amplitude motion of the drive shaft 16 when placed under user loading. User loading refers to a user brushing his or her teeth with the brush-head 18 attached to the drive shaft 16 being reciprocated via the drive system 22.

In one embodiment, drive system 22 preferably comprises a resonant motor having a floating shaft that is suspended axially and rotationally within the motor by means of a permanent magnetic field. The field is preferably established with permanent magnets arranged within the motor casing. A distal end of the drive shaft 16 extends through the motor casing and through the top of the power toothbrush handle 14 when installed therein, the distal end being configured for attachment of a brush-head or other appliance. In one embodiment, the distal end of the drive shaft 16 is configured to extend through the motor casing toward the proximal end of the handle 14. The proximal end of the drive shaft 16 preferably includes at least one inertial weight member 24 coupled thereto, as will be discussed further herein.

Figure 6:
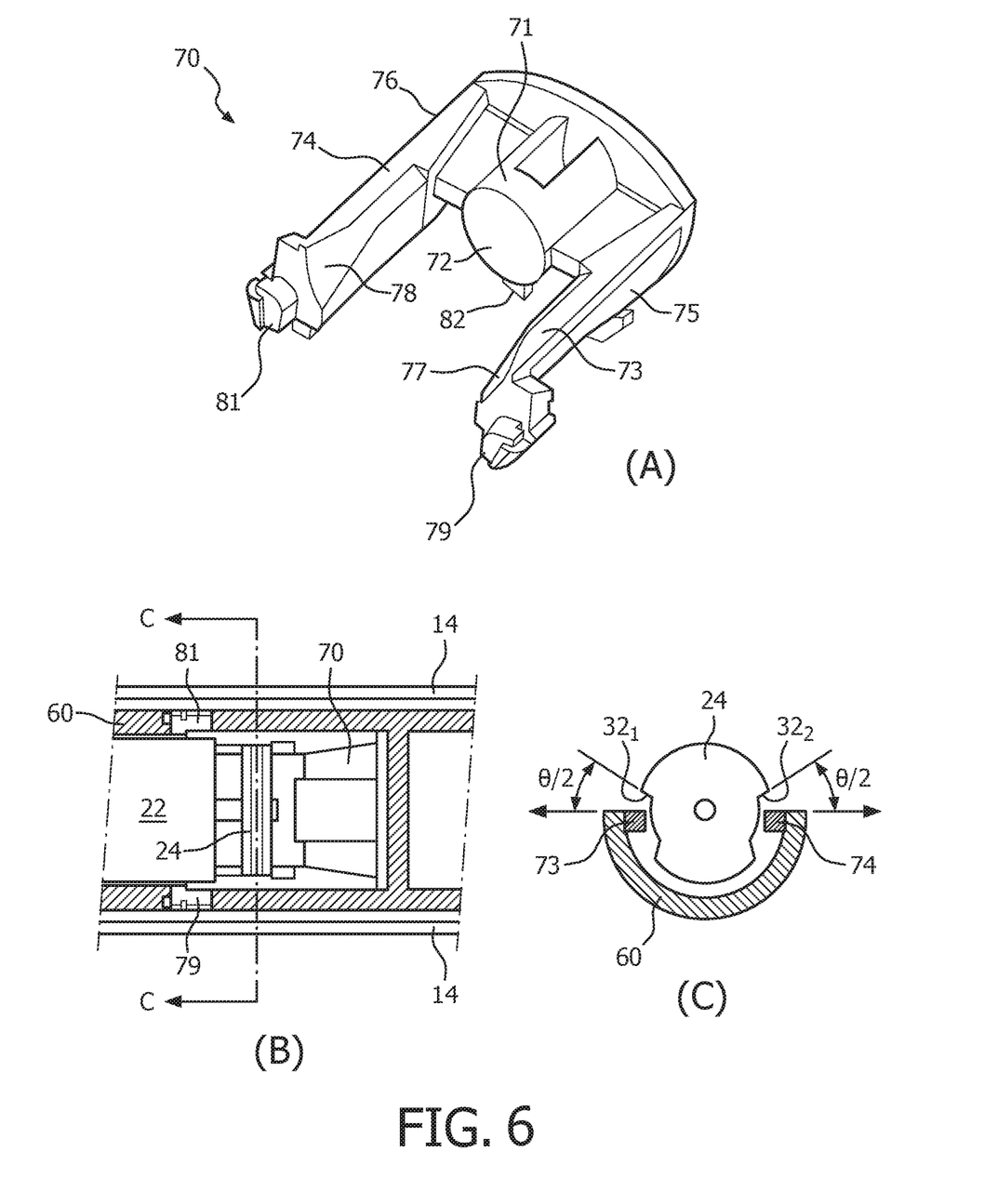
FIGS. 6(A), 6(B), and 6(C) illustrate a perspective view, side cross-sectional view, and sectional view, respectively, of a resilient motor mount for a resonating motor in a power toothbrush, according to an embodiment of the present disclosure.

In addition, with reference still to FIG. 1, drive system 22 is coupled within handle 14 via at least two components, which include (i) a frame 60 (shown in FIG. 6) arranged within handle 14 and (ii) a resilient motor mount 70, as will be discussed further in connection with FIG. 6. As will be described in more detail, the motor mount 70 is arranged to be axially spaced away from the proximal end of drive shaft 16 by an amount "d" when assembled. Motor mount 70 further provides axial shock protection in the device, e.g., as against an axial shock induced by a force F applied to distal end of drive shaft 16.

Figure 2:
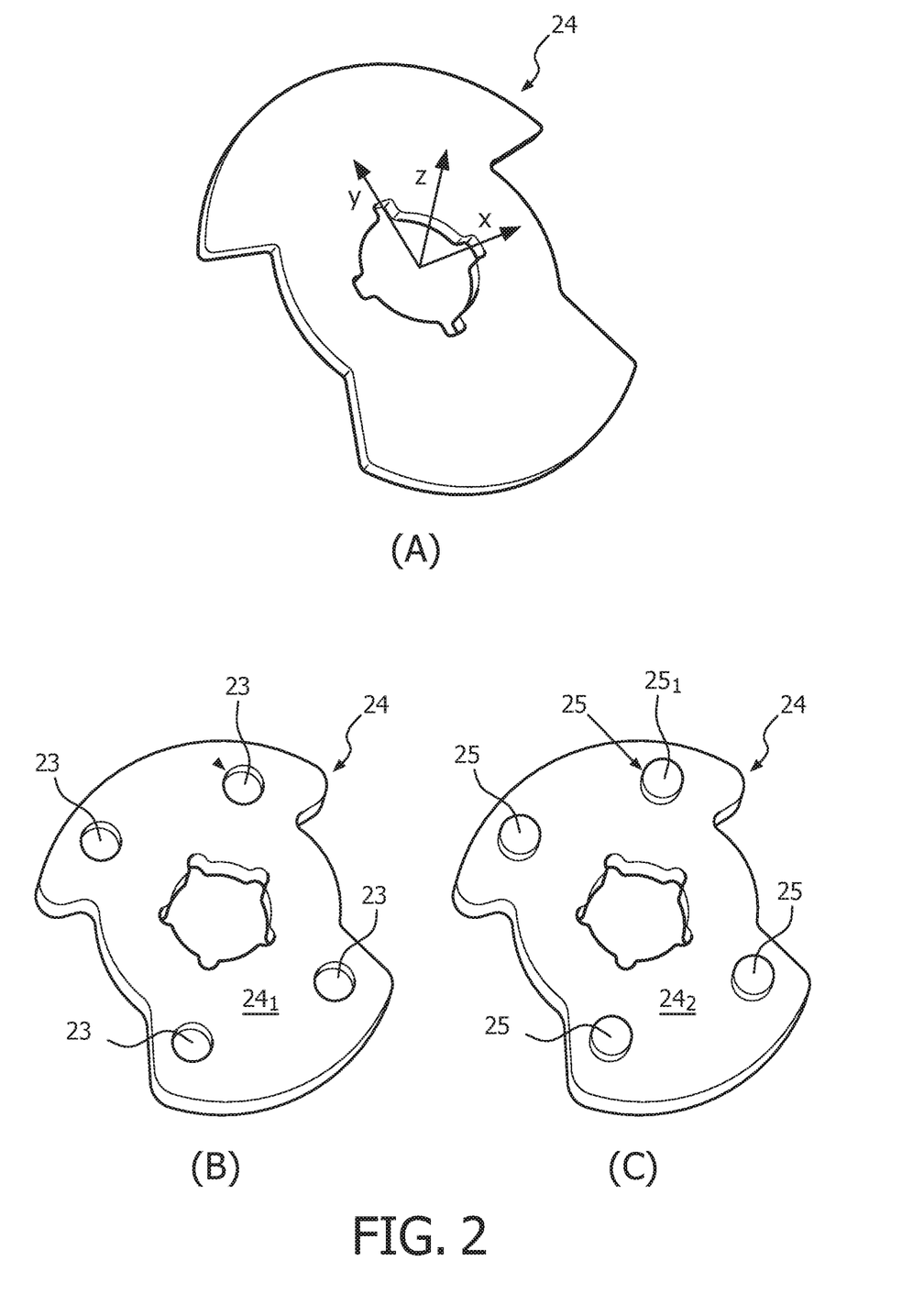
FIGS. 2(A), 2(B), and 2(C) are perspective diagram and image views of a single inertial weight member according to an embodiment of the present disclosure.

Turning now to FIG. 2 (2(A), 2(B), 2(C)), a perspective diagram view of an inertial weight member 24 according to an embodiment of the present disclosure is shown. The inertial weight member 24 comprises a planar material having a complex shape balanced along an x-, y- and z-axis, shown in FIG. 2(A). In one embodiment, the inertial weight member 24 comprises any suitable high-density material with a strength equal to or greater than aluminum. For example, the suitable high-density material can comprise stainless steel, mild steel, iron, sintered iron, cast iron, cast aluminum, and/or aluminum. Other materials, including non-metallic materials, may also be possible. In one embodiment, the single inertial weight member 24 comprises a plurality of recesses and dimples formed in or on opposing generally planar surfaces, respectively, of the inertial weight member. The plurality of recesses and dimples advantageously provide for co-location and lamination of a plurality of individual inertial weight members together, without additional requirements. As shown in FIG. 2(B), on a first generally planar surface $24_1$, a plurality of recesses 23 are formed within the surface, using any suitable well known technique. As shown in FIG. 2(C), on a second generally planar surface $24_2$, opposite the first generally planar surface $24_1$, a plurality of dimples 25 are formed within the surface, using any suitable well known technique.

In one embodiment, the plurality of recesses 23 and the plurality of dimples 25 comprise a same number within each plurality. For example, the plurality of recesses 23 in surface $24_1$ can include four recesses, while the plurality of dimples 25 in surface $24_2$ can include four dimples. When laminated together, the plurality of recesses 23 on a first inertial weight member are configured to match and/or mate with a complementary plurality of dimples 25 on a second adjacent inertial weight member to secure the first inertial weight member to the second inertial weight member in a given configuration/orientation. Additional inertial weight members are added to the first two in a similar manner, to achieve a desired added inertial resonant system implementation. While FIGS. 2(B) and 2(C) illustrate four recesses and four dimples in a certain configuration, other configurations and numbers of recesses and dimples are also possible. The recesses and dimples advantageously provide for co-location, assembly, and the securing together of a plurality of inertial weight members for a given implementation.

Figure 3:
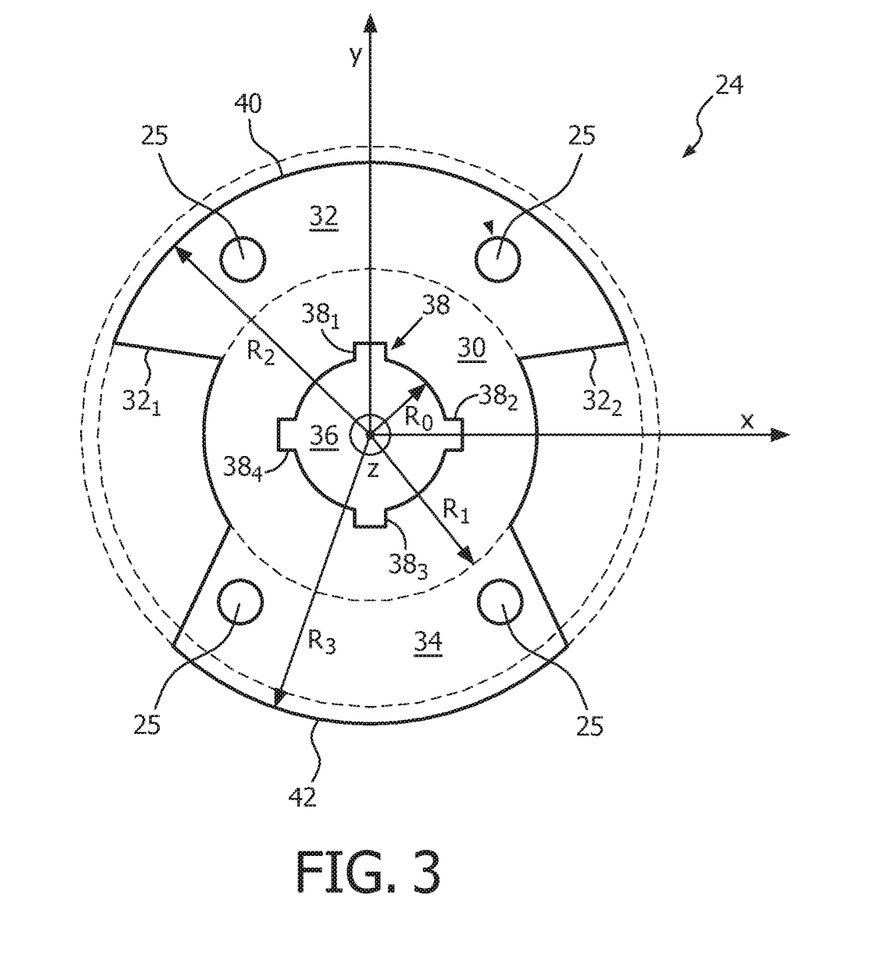
FIG. 3 is a two-dimensional representation view of the single inertial weight member of FIG. 2 viewed along the z-axis according to an embodiment of the present disclosure.

Referring now to FIG. 3, a two-dimensional representational view of an inertial weight member 24 of FIG. 2 is shown, viewed along the z-axis. As illustrated, the complex shape of the inertial weight member 24 includes an inner portion 30, a first outer portion 32 extending from the inner portion 30 in a first direction, and a second outer portion 34 extending from the inner portion 30 in a second direction, opposite the first direction. In other words, the first outer portion 32 extends from the inner portion 30 in a positive direction along the y-axis and the second outer portion 34 extends from the inner portion 30 in a negative direction along the y-axis.

With reference still to FIG. 3, the inner portion 30 includes a mounting aperture 36 having a principal diameter (i.e., having a radius $R_0$) configured for being mounted, e.g., via a press fit, onto the drive shaft 16 (FIG. 1) along the principal axis 26. The mounting aperture 36 further includes at least one attachment feature 38 configured for coupling the inertial weight member 24 via a press fit onto a complementing feature (not shown) of the drive shaft 16 in a given radial orientation with respect to the principal axis 26. In a further embodiment, the at least one attachment feature 38 comprises equally spaced features about an inner perimeter of the mounting aperture 36 in the inner portion 30 of the inertial weight member 24. For example, the at least one attachment feature 38 comprises four equally spaced features as indicated by reference numerals $38_1$, $38_2$, $38_3$ and $38_4$. In addition, the at least one attachment feature 38 can comprise a cut-out, or other suitable feature, within the material of the inertial weight member 24. While FIG. 3 illustrates four cut-outs in a certain configuration, other configurations and numbers of attachment features are also possible.

The first outer portion 32 of the complex shape provides a first additional weight located between a first ($R_1$) and second ($R_2$) radial distance away from the center of rotation (i.e., corresponding to principal axis 26). The second outer portion 34 of the complex shape provides a counter-balanced additional weight located between the first radial distance ($R_1$) and a third radial distance ($R_3$), wherein the third radial distance ($R_3$) is greater than the second radial distance ($R_2$) around the z-axis (labeled "Z" in FIG. 3). Furthermore, a perimeter 40 of the first outer portion 32 at the second radial distance ($R_2$) is greater than a perimeter 42 of the second outer portion 34 at the third radial distance ($R_3$).

Figure 4:
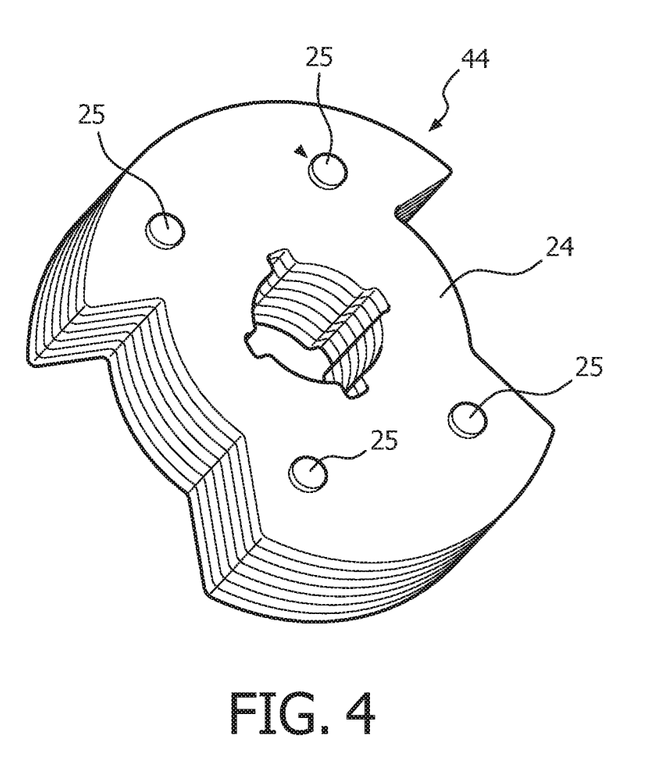
FIG. 4 is a perspective diagram view of a laminated stack of a plurality of single inertial weight members according to another embodiment of the present disclosure.

Turning now to FIG. 4, a perspective diagram view of a laminated stack 44 of inertial weight members 24 according to another embodiment of the present disclosure is shown. In one embodiment, the laminated stack 44 of FIG. 4 includes seven single inertial weight members 24. However, the specific number of single inertial weight members 24 in a given laminated stack 44 is determined according to the requirements of a given implementation of the added inertia resonant system for a power toothbrush 10. In addition, each of the inertial weight members 24 of the laminated stack 44 is properly aligned with one another and securely held together via mating of complementary recesses and dimples, as discussed earlier herein with reference to FIGS. 2(B) and 2(C). Accordingly, the laminated stack 44 also comprises a complex shape balanced along the x-, y- and z-axis.

Figure 5:
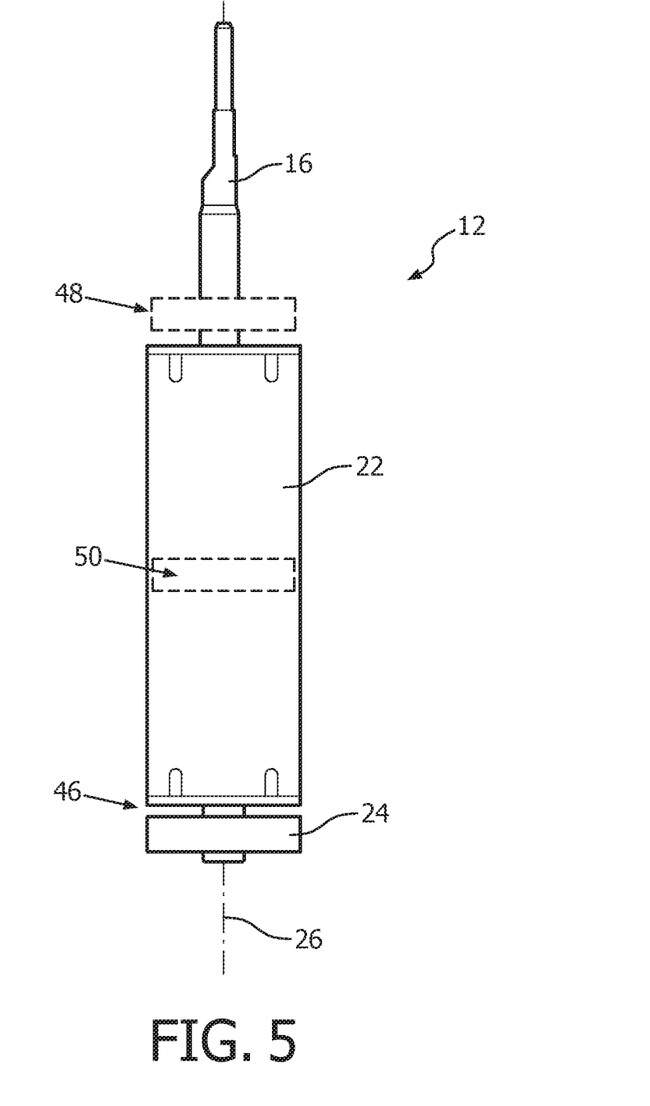
FIG. 5 is a diagram view of an added inertial weight member located at at one of the front, middle, or rear of the drive system of a power toothbrush according to an embodiment of the present disclosure.

With reference to FIG. 5, a diagram view of the added inertial weight member 24 can be located at one of the front, middle, or rear of the drive system 22, as is generally indicated by reference numerals 48, 50 and 46, respectively.

With reference now to FIGS. 6(A), 6(B), and 6(C), there is illustrated a perspective view, side cross-sectional view, and sectional view, respectively, of the resilient motor mount 70, according to an embodiment of the present disclosure. Resilient motor mount 70 is particularly characterized by having features which are arranged to limit a maximum displacement of the associated motor shaft, in either of a rotational displacement or along the shaft axis. Motor mount 70 is also disposed to be in a compressive arrangement between the motor 50 and a side surface of either of the frame 60 or the handle 14.

The FIG. 6A embodiment is a resilient motor mount 70 having a bottom bumper 71 and first and second mount arms, indicated by reference numerals 75 and 76, respectively. Bottom bumper 71 further includes an axial stop surface 72, wherein the axial stop surface 72, which is disposed in a spaced away facing orientation to the proximal end of drive shaft 16, when the resilient motor mount 70 and motor 22 are coupled together within frame 60 and handle 14. FIG. 6B illustrates such an arrangement. Bottom bumper 71 functions to limit the axial displacement of the shaft end, and to absorb energy from the shaft end striking the bumper 71.

Motor mount 70 also includes one or more mount arms, as indicated by reference numerals 75 and 76. Mount arms 75 and 76 are disposed in a compressive arrangement between the motor 22 and an inner side surface of frame 60. Each of the mount arms 75 and 76 include a respective compression surface, indicated by reference numerals 77 and 78, which is shaped to receive a portion of the proximal end of motor 22, as shown in FIG. 6B.

For descriptive purposes, bottom bumper 71 has a central axis and a periphery, the central axis generally being aligned perpendicular to and passing through the center of stop surface 72. In the illustrated embodiment, each of the first and second mount arms 75 and 76 are disposed outside of the periphery and extending away from the periphery in a direction along the central axis. Each mount arm further includes a cogging stop surface, indicated by reference numerals 73 or 74, and a mount tab, indicated by reference numeral 79 or 81. An additional mount tab 82 may be included on bottom bumper 71. As can be seen, the resulting resilient motor mount 70 is generally u-shaped and comprises a unitary piece of elastomeric material, such as rubber or plastic.

The functions of the stops and mount tabs are further detailed with reference to FIG. 6B. First, the axial stop surface 72 is disposed in a spaced away distance "d" (FIG. 1) from the proximal end of the motor drive shaft 16. This arrangement allows for free rotation and axial vibration for normal toothbrush operation without undue friction losses. Under axial shock or excessive force however, the bottom bumper 71 and shaft end 16 may come into contact, which opposes further displacement of the drive shaft in the axial direction. Such displacement can be induced by dropping the toothbrush 10 or by excessive force in pressing a brush head onto the distal shaft end. In the latter case, the spaced away distance should be less than a displacement that is caused by the operation of receiving the toothbrush head onto the drive shaft. Alternatively, the spaced away distance should be smaller than a pole-slipping distance from the axial magnetic rest position to prevent axial pole slippage. Alternatively, the spaced away distance should be smaller than a distance between a pole element on the floating drive shaft and a back end casing surface of the motor, to prevent motor damage.

Mount tabs 79, 81, and 82 prevent the rotation of the resilient motor mount 70 within the frame 60 during operation. Corresponding complementary slots located in frame 60, or alternatively in handle 14, receive the mount tabs 79, 81 such that a coupling engagement there between secures and advantageously prevents any rotation displacement of the resilient motor mount 70 within the frame 60. In the FIG. 6 embodiments, mount tabs 79 and 81 are arranged generally opposite compression surfaces 77 and 78, respectively, on the mount arms 75, 76. Tab 82 is located at the base of bottom bumper 71.

The resilient motor mount 70 includes cogging stop surfaces, indicated by reference numerals 73 and 74, disposed at a radial distance from the drive shaft axis. Cogging stops 73 and 74 interact with corresponding stop surfaces, indicated by reference numerals $32_1$ and $32_2$, of the first outer portion 32 of the at least one added inertia weight member 24 when disposed on the proximal end of drive shaft 16 in conditions of excessive force to prevent excessive rotation of the drive shaft. By limiting the rotational displacement of the drive shaft within a desired range, the cogging stops advantageously prevent a permanent cogging rotational displacement that can occur when a shaft pole undesirably skips (or is undesirably rotationally displaced) to a next stator magnet position.

As illustrated in the section view of FIG. 6B at FIG. 6C, the cogging stops 73 and 74 are arranged at an angular displacement from corresponding stop surfaces $32_1$ and $32_2$, respectively, of the added inertial weight member 24. During normal resonating operation, such as up to a total displacement of 11 degrees, no contact will occur between cogging stops 73, 74 and the stop surfaces $32_2$ of the added inertial weight member 24. However, the cogging stops 73, 74 will prevent additional angular motion beyond a predetermined angular limit, such as theta/2, in either direction induced, for example, by a forced twisting of the drive shaft on the appliance.

Although only a few exemplary embodiments have been described in detail above, those skilled in the art will readily appreciate that many modifications are possible in the exemplary embodiments without materially departing from the novel teachings and advantages of the embodiments of the present disclosure. For example, the embodiments of the present disclosure can be advantageously implemented in various reciprocating motor designs with weights as needed to achieve amplitude and power consumption specifications while under user loading in power toothbrush applications. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements, and/or by means of a suitably programmed computer. In a device claim enumerating several means, several of these means may be embodied by one and the same item of hardware. The mere fact that certain measures are recited in mutually different dependent claims does not indicate that a combination of these measures cannot be used to an advantage.

The invention claimed is:

1. An added inertia resonant system for a power toothbrush to achieve low power, high amplitude motion of a drive shaft when placed under user loading, comprising:
    a drive shaft having a principal axis that defines a center of rotation;
    a drive system configured to impart a reciprocating motion to said drive shaft about the principal axis; and
    at least one inertial weight member coupled to the drive shaft, wherein the at least one inertial weight member comprises a single planar material extending in an x-y plane about a central z-axis and being balanced in the x and y directions;
    wherein the at least one inertial weight member includes a first portion extending to a first distance radially in a first direction in the x-y plane, and a second portion extending to a second distance radially in a second direction in the x-y plane, the first distance being different from the second distance, and wherein the at least one inertial weight member includes an inner portion, a first outer portion extending from the inner portion in a first direction, and a second outer portion extending from the inner portion in a second direction, opposite the first direction.

2. The system of claim 1, wherein the inner portion includes a mounting aperture having a principal diameter configured for being mounted onto the drive shaft along the principal axis.

3. The system of claim 2, wherein the mounting aperture further includes at least one attachment feature configured for coupling the inertial weight member via a press fit onto a complementing feature of the drive shaft in a given radial orientation with respect to the principal axis.

4. The system of claim 1, wherein the first outer portion of the at least one inertial weight member comprises a first additional weight located between a first and second radial distance away from the center of rotation, and the second outer portion of the at least one inertial weight member comprises a counter-balanced additional weight located between the first radial distance and a third radial distance, wherein the third radial distance is greater than the second radial distance around the z-axis, and further wherein a length of an edge of the first outer portion at the second radial distance is greater than a length of an edge of the second outer portion at the third radial distance.

5. The system of claim 4, further comprising a resilient mount and a frame, wherein the drive system is coupled to the frame via the resilient mount, the resilient mount including rotational displacement cogging stop surfaces, and wherein the first outer portion of the at least one inertial weight member further comprises first and second rotation stop surfaces, wherein the first and second rotation stop surfaces are configured for engagement with the cogging stop surfaces of the resilient mount to limit a rotational displacement of the drive shaft within a desired range.

6. The system of claim 1, wherein the at least one inertial weight member further comprises recesses and dimples formed in or on planar surfaces of the at least one inertial weight member that co-locate and secure a plurality of inertial weight members together as a lamination to increase a total weight for a desired total inertial mass.

7. The system of claim 1, wherein the low power, high amplitude motion comprises a power on the order of <4 W and an amplitude of up to 20 degrees full motion about the center of rotation.

8. A power toothbrush, comprising:
    the added inertia resonant system of claim 1; and
    a brush head member adapted for being coupled in a removable fashion to a distal portion of the drive shaft.

* * * * *